United States Patent
Ashman et al.

(10) Patent No.: US 6,413,089 B1
(45) Date of Patent: Jul. 2, 2002

(54) IMMEDIATE POST-EXTRACTION IMPLANT

(75) Inventors: Arthur Ashman, 153 Bayberry La., Westport, CT (US) 06880; Leonard I. Linkow, Fort Lee, NJ (US)

(73) Assignee: Arthur Ashman, Westport, CT (US)

( * ) Notice: Subject to any disclaimer, the term of this patent is extended or adjusted under 35 U.S.C. 154(b) by 0 days.

(21) Appl. No.: 09/248,079

(22) Filed: Feb. 10, 1999

(51) Int. Cl.[7] .................................................. A61C 8/00
(52) U.S. Cl. ...................................... 433/174; 433/173
(58) Field of Search ................................ 433/172, 173, 433/174, 175, 176, 201.1

(56) References Cited

U.S. PATENT DOCUMENTS

| | | | |
|---|---|---|---|
| 2,609,604 A | 9/1952 | Sprague | 433/174 |
| 3,499,222 A | 3/1970 | Linkow et al. | 433/174 |
| 4,521,192 A | 6/1985 | Linkow | 433/173 |
| 4,629,464 A * | 12/1986 | Takata et al. | 623/16 |
| 4,713,004 A | 12/1987 | Linkow et al. | 433/174 |
| 4,738,623 A * | 4/1988 | Driskell | 433/173 |
| 5,246,370 A * | 9/1993 | Coatoam | 433/173 |
| 5,310,343 A * | 5/1994 | Hasegawa et al. | 433/173 |
| 5,344,457 A * | 9/1994 | Pilliar et al. | 433/174 |
| 5,478,237 A * | 12/1995 | Ishizawa | 433/174 |
| 5,533,898 A * | 7/1996 | Mena | 433/173 |
| 5,588,838 A * | 12/1996 | Hansson et al. | 433/174 |
| 5,642,996 A * | 7/1997 | Mochida et al. | 433/174 |
| RE35,784 E | 5/1998 | Linkow et al. | 433/174 |
| 6,132,214 A | 10/2000 | Suhonen et al. | 433/201.1 |

* cited by examiner

Primary Examiner—John J. Wilson
(74) Attorney, Agent, or Firm—Darby & Darby

(57) ABSTRACT

A submergible or non-submergible ("one stage") screw-type implant for use in the immediate post-extraction site of a patient's tooth. In order to increase the ability of regenerated bone to anchor the implant, an upper portion of the implant has a preferably generally conical shape and has a plurality of spherical projections sintered to its outer surface to make it suitable for bone integration and retention. The lower portion of the implant has a cylindrical shape with threads extending over a portion thereof. A channel is located through the threads and is shaped so that one side forms a cutting edge that makes the lower portion of the implant self-tapping into the bone at the base of the tooth extension socket.

34 Claims, 6 Drawing Sheets

IMMEDIATE POST-EXTRACTION IMPLANT

TECHNICAL FIELD

This invention relates generally to dental implants, and, more particularly, to submergible screw-type implants.

BACKGROUND ART

Screw-type implants are well known in the art. U.S. Pat. No. 3,499,222 of L. I. Linkow et al. (the "'222 patent") discloses screw-type implants that may be buried in the alveolar ridge crest bone of a patient in an edentulous region. The implant has a threaded lower portion that may be screwed into an opening created in the bone after the tissue has been displaced. A coronal portion protrudes above the bone and is used to support an artificial dental appliance, e.g., an artificial tooth or bridge.

More recently, submergible implants have been created in which the threaded portions of the implants can be completely embedded in the bone. They may then be covered with tissue and allowed to remain in place while new bone grows around the implant and through vent holes in it. Once it is firmly anchored in new bone, the tissue is reopened and an upper post portion is screwed into the implant portion and is used to mount the artificial dental device. An example of this type of implant can be found in U.S. Pat. No. 4,713,004 of L. I. Linkow et al. (the "'004 patent").

A prior surgical method for installing an implant portion involved creating an incision in the tissue covering the alveolar ridge crest bone. This underlying bone was then exposed and a cylindrical bore was drilled into the bone at a depth sufficient to hold the implant portion of the device. The bore was made slightly smaller in diameter than the implant device and was at an angle that would allow it to engage the major portion of the available bone. Then a bore tap is used to create threads in the bore, after which the implant device was threaded into the remaining bone.

Alternatively, an implant may be embedded and not covered with tissue. This eliminates the need to reopen the tissue later to mount an artificial dental device.

It is also well known in the art, e.g., from the '004 patent, that a channel through threads on the implant will create a cutting edge so the implant becomes self-tapping (e.g., end cutting). When installing an implant portion in the patient's bone, it is advantageous if the implant is self-tapping because it causes the implant to be anchored more securely. If such a self-tapping implant is used, a bone tap is not needed and the implant is threaded directly into the bone utilizing the self-tapping threads created by the channel along the length of its threads.

Also, it is advantageous if the bone chips created during a self-tapping operation are deposited into the bore or opening, because these autogenous chips promote faster bone regenerative growth. The channel guides these bone chips, which are created during the self threading of the implant, toward the base of the bore in the bone. In particular, during the insertion procedure with a self-tapping implant, bone chips are removed from the walls of the bore while forming the grooves in the bone that match the threads in the implant. These bone chips drop along the channel to the base of the bore and help to promote the growth of new bone that firmly anchors the implant in place.

When a tooth is extracted, it leaves behind a rather large conically-shaped cavity, which does not lend itself to the insertion of a cylindrical implant if an artificial tooth is to be substituted for the removed tooth. One technique for overcoming this problem of the extracted tooth is to expose the cavity in the bone, fill the extraction site with bone graft material, such as autogenous, allographic or xerographic material, and then cover the site with gum tissue for a period of time sufficient for new bone to grow into and fill the cavity, e.g., with a mixture of the grafted bone and newly grown bone. Then a cylindrical bore is drilled at the site and a dental implant is installed in the usual manner. However, this requires that the patient live with an edentulous area without a functional prosthesis for a long period of time.

As an alternative, the implant can have a shape that is not cylindrical, but instead is conical or U-shaped, in order that it more nearly fits the dimensions of an extraction site. Such implants may be found in U.S. Pat. No. 4,521,192 of L. I. Linkow (the "'192 patent"), and U.S. Pat. No. 2,609,604 of B. F. Sprague (the "'604 patent"). As the slope of the conical shape of the extraction site cannot be predicted in advance, these implants cannot be made self tapping. As a result, no pressure can be applied to these implants for a significant period of time, i.e., until existing bone has grown around the implant to anchor it in place. In addition, as a self-tapping implant is not used, there may not be intimate contact between the implant and the new bone, so the implant may eventually fail, even if a significant amount of time is allowed to pass before an artificial tooth is mounted on the implant and it is put into use.

It would be of great benefit when replacing extracted teeth with dental implants to use an implant that compensates for the shape of the extraction socket, is at least partially self-tapping for initial implant stability and assures relatively intimate contact between the implant and new bone so that the implant can be put into service relatively soon after the procedure and still have a low probability of subsequent failure.

SUMMARY OF THE INVENTION

The present invention is directed to a dental implant that may be used at the site of a recent tooth extraction and can be put into service in a reasonably short period of time. This implant has a lower self-tapping portion and an upper portion covered with a sintered material that is osteopromotive and osteoretentive so to promote adhesion between the implant and the surrounding bone.

In a preferred form of an illustrative embodiment, the implant is of the submergible screw type with an upper portion having a conical shape and a lower cylindrical portion having threads. A longitudinal channel or slot extends through the threads on the lower cylindrical portion so as to make the threads self-tapping. The channel is wider toward its apical end.

One side of the channel is at a right angle or acute angle to the implant circumference so as to create a cutting edge that forms the self-tapping capability for the implant. The other side of the channel can be at an oblique angle to the circumference.

At least a portion of the exterior surface of the upper conical portion of the implant is sintered with a plurality of spherical projections made of a material suitable for bone integration, the spaces in between forming a porous surface.

At the lower or apical portion of the implant there is a vent or opening to allow for autogenous bone chips created during self-tapping to enter therein when the implant is screwed into the bone socket.

BRIEF DESCRIPTION OF THE DRAWINGS

The foregoing and other features of the present invention will be more readily apparent from the following detailed description and drawings of an illustrative embodiment of the invention, in which.

DESCRIPTION OF ILLUSTRATIVE EMBODIMENTS

The design requirements for dental implants placed into immediate extraction sites differ significantly from the design of general implants used presently for placement in edentulous jawbones. Today all implants used in immediate extraction sites are either threaded, coated with a surface material or sintered. However, these implants do not provide the best design for immediate fresh extraction sites. Such immediate extraction sites require an implant designed specifically to address the morphology of the bony defect created during the extraction of a tooth.

Figure 1:
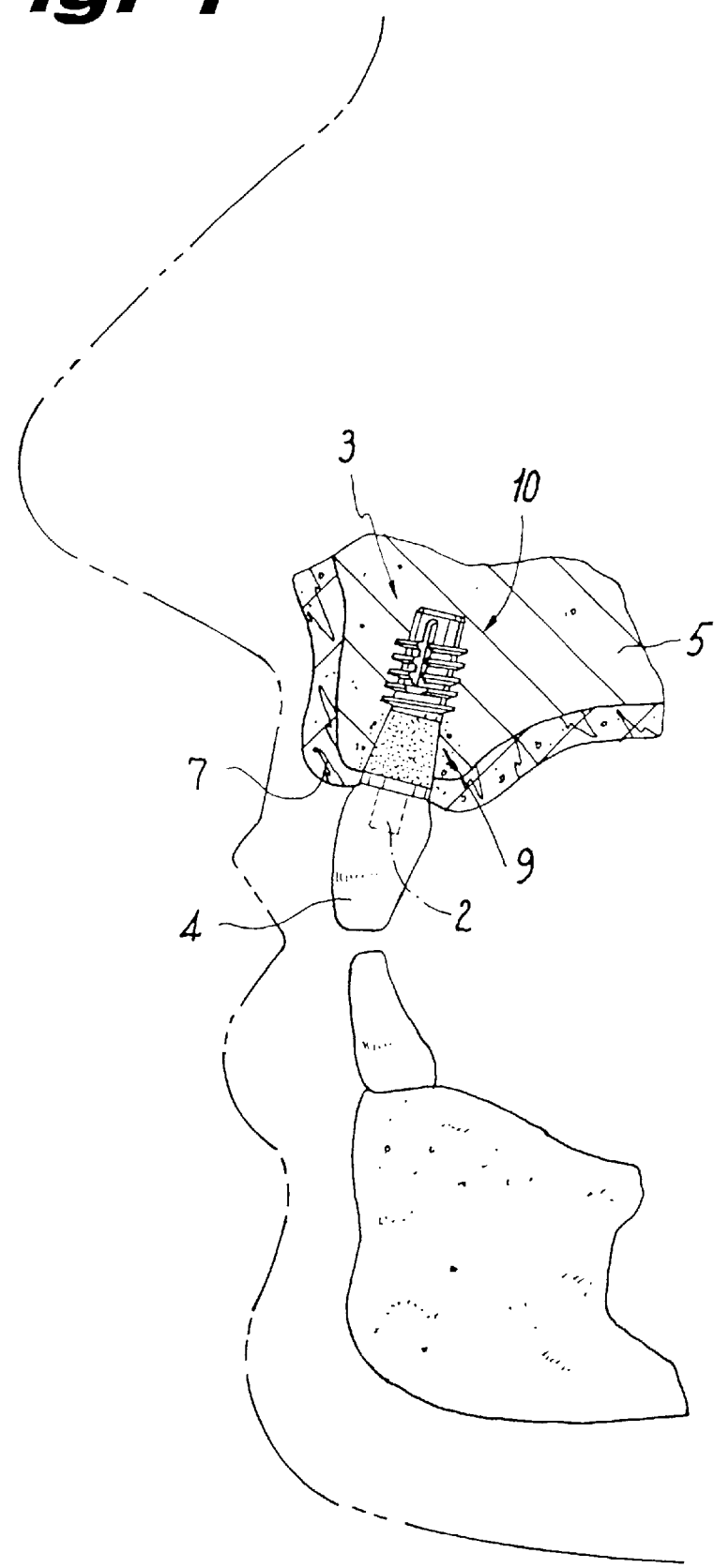
FIG. 1 is a schematic cross section of the side of a patient's face showing the alveolar ridge crest with a screw type implant according to the present invention installed therein.

The implant system of the present invention is at least a two part screw-type dental implant 3 (FIG. 1), having a threaded cylindrical lower portion 10 that is buried in the bone 5 of the patient and an upper portion 9, preferably generally conically-shaped, that is attached thereto. The upper portion 9 is covered by soft tissue 7. A post or abutment 2 is shown in dotted line extending from upper portion 9 and supporting an artificial tooth structure 4 to complete the implant system. As shown in FIG. 1 the implant screw lower portion 10 is located in a bore in the alveolar crest bone 5, at an angle that causes it to be in the center of the thickest portion of good available bone. The abutment 2 is attached both to the implant portion and the artificial tooth 4 and may have an angular offset to the implant so that the artificial tooth is in proper alignment with the rest of the teeth.

Figures 2, 3:
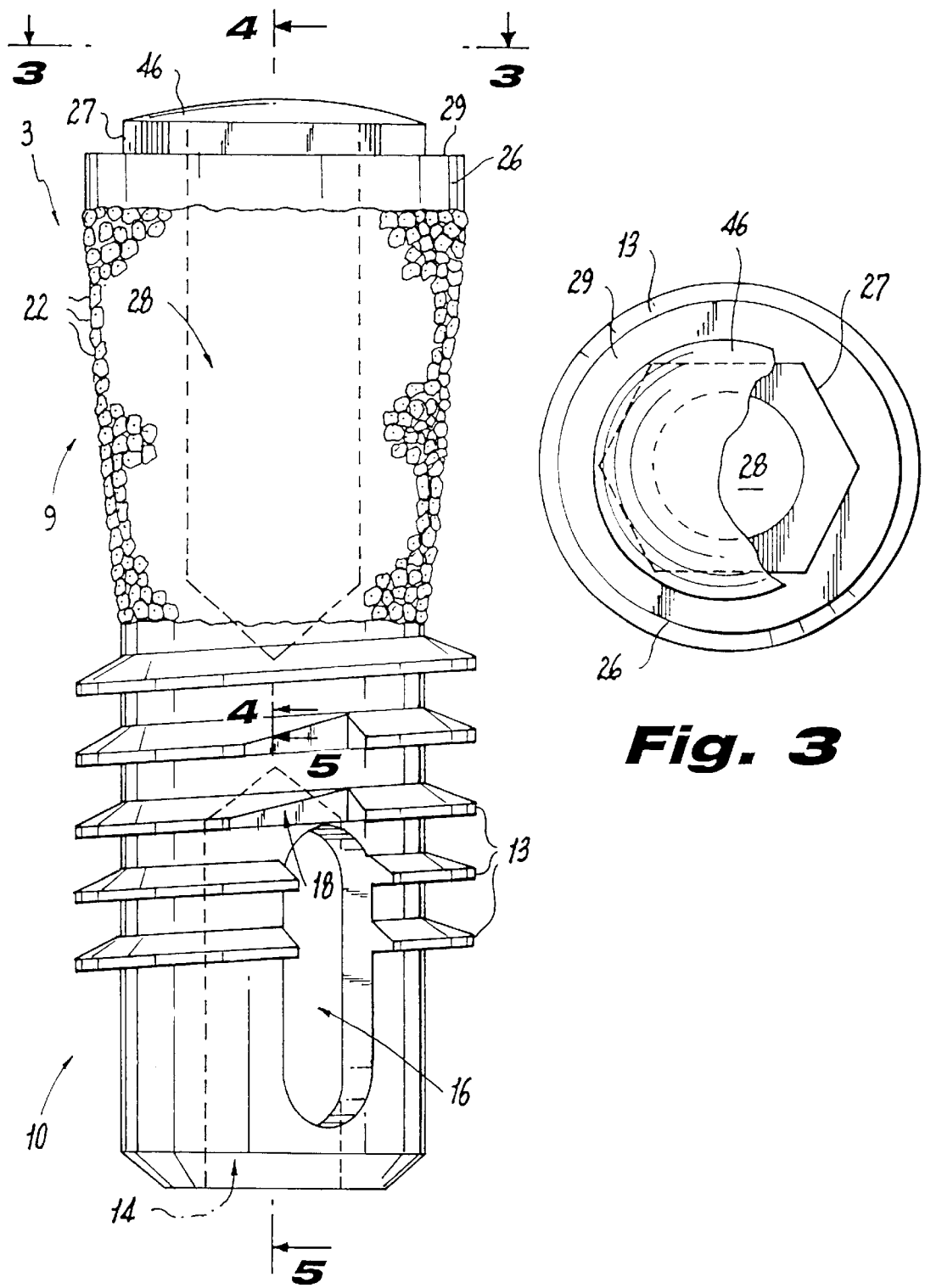
FIG. 2 is an enlarged view of an illustrative embodiment of the implant portion of the device of FIG. 1.
FIG. 3 is a top view of the implant portion of FIG. 2.
Figure 4:
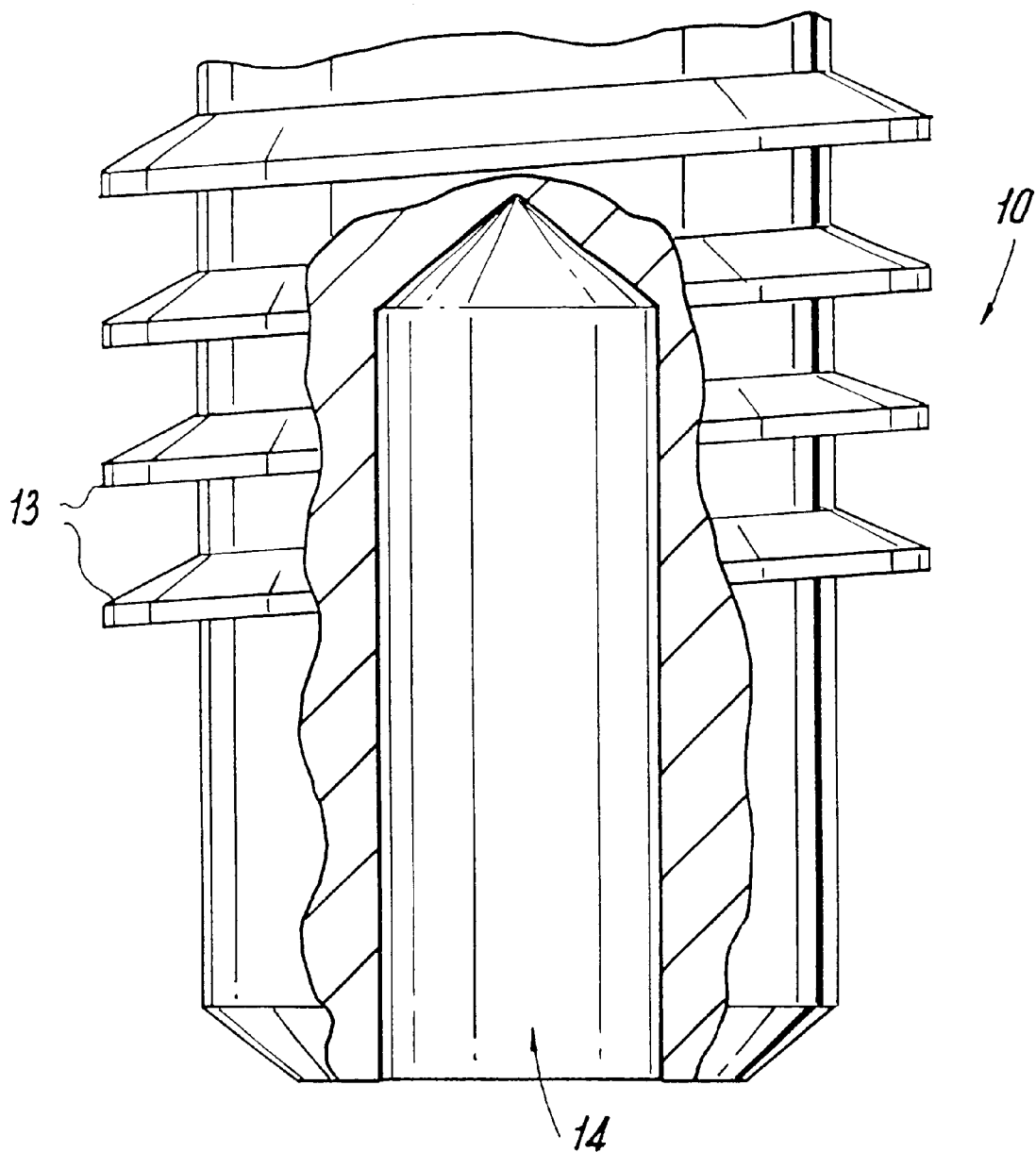
FIG. 4 is a cross-sectional view through the implant portion of FIG. 2 along line 4—4 and longitudinally down the centerline of FIG. 3 depicting the cross-sectional shape of the lower implant portion according to the present invention.
Figure 5:
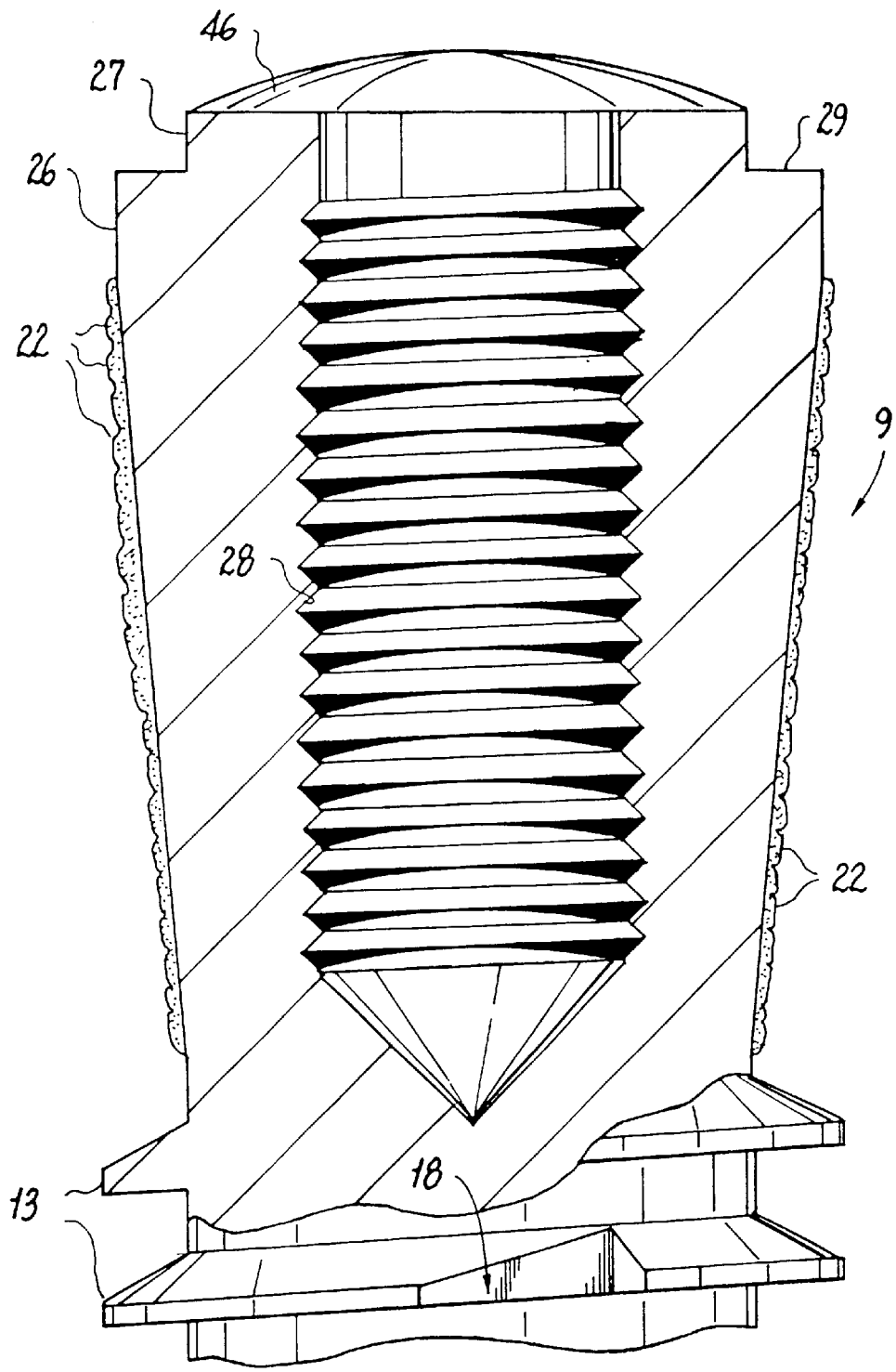
FIG. 5 is a cross-sectional view through the implant portion of FIG. 2 along line 5—5 and longitudinally down the centerline of FIG. 3 depicting the cross-sectional shape of the upper implant portion according to the present invention.

In FIGS. 2, 4 and 5, the screw implant 3 of FIG. 1 is illustrated in more detail. This screw implant portion contains threads 13 in the lower portion 10 that extend over the top two-thirds of this lower portion 10. These threads may have a flat bottom and be angled up to form a Christmas tree shape in cross section. The lower half of the implant portion 10 contains a cavity 14, as can be seen in FIG. 4. This cavity is open at its bottom. Also, spaced about the lower end of the implant portion 10 are holes or vents 16, which penetrate from its exterior to the interior cavity 14. The purpose of these vents is to allow new bone to grow through and into the center cavity 14 in order to firmly anchor the implant in the patient's bone 5.

A channel 18 in alignment with at least one vent 16 extends through most of the threads, but not the top thread. The channel does not pass through the top thread in order to prevent tissue from growing down the channel. This channel has two purposes. First, the channel 18 and the vent 16 create cutting edges on the adjacent threads that make the implant self tapping. Also, the channel provides a path by which bone chips created during the threading of the implant into the bone may pass down to the vent 16 and enter the cavity 14 where they promote the growth of new bone. To facilitate this, the channel 18 widens toward the bottom of the implant. These features are described in U.S. Pat. No. 4,713,004, which is incorporated herein by reference.

Figure 7:
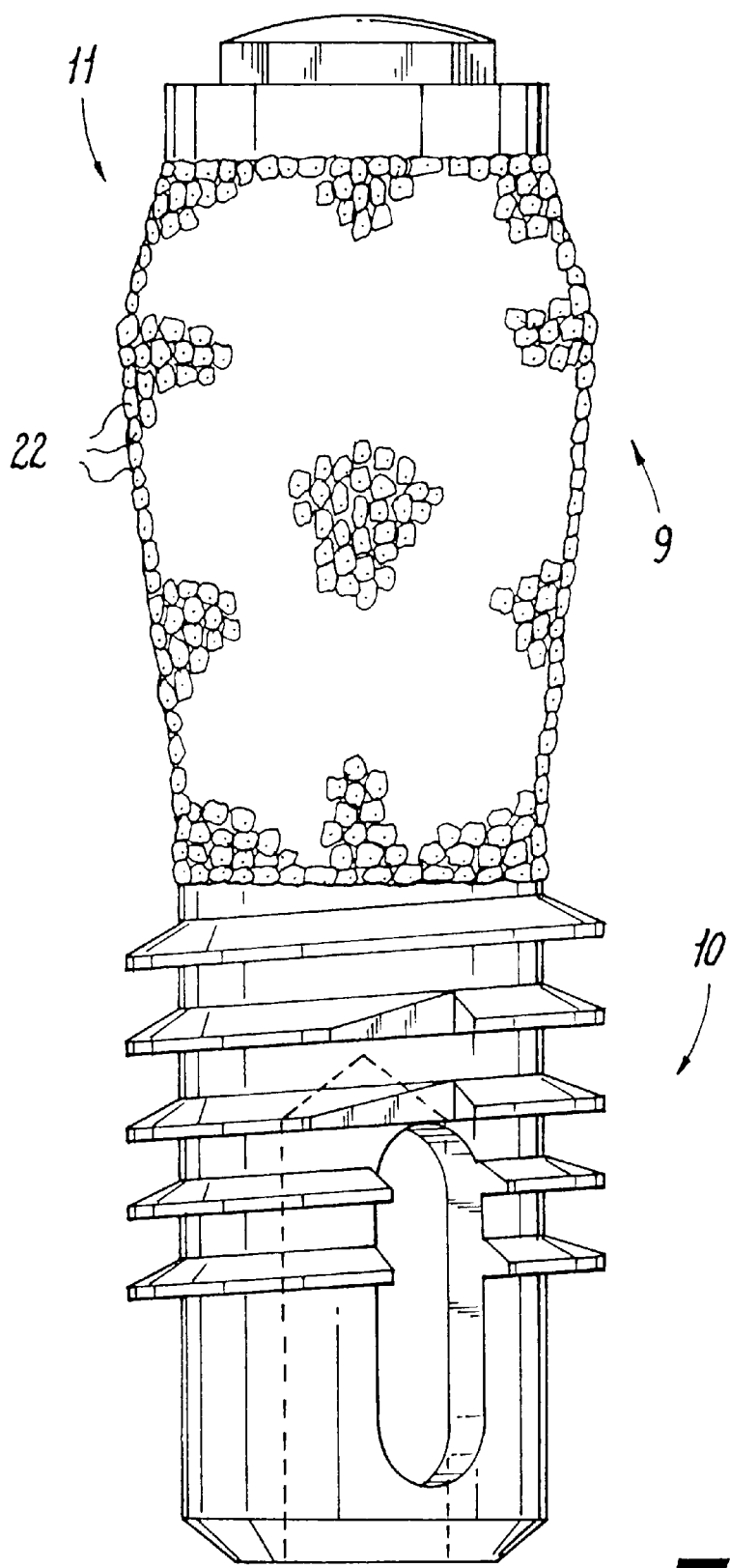
FIG. 7 is an enlarged view of another illustrative embodiment of the implant portion of the device of FIG. 1.

The upper portion 9 of the screw implant 3 preferably has a generally conical or fluted shape. For example, the base of portion 9 where it contacts portion 10 may have a diameter of about 3.0 mm, while the top of the portion 9 may have a diameter of about 3.5 mm. In a preferred embodiment shown in FIG. 7 the upper end 11 of the upper portion 9 is tapered upwardly. This provides a more gently contoured surface to minimize soft tissue irritation.

In FIG. 5 the upper part of the implant portion is shown partly broken away and partly in section to illustrate an interior cavity 28 and the shape of the threads 13. The top surface 29 (FIG. 2) of the conically-shaped upper implant portion 9, has a disk-shaped transition cap 26 from which there extends a hexagonally-shaped projection 27, as shown more clearly in FIG. 3. This hexagonal shape allows a tool, e.g., a wrench, to be used to rotate the implant portion so as to thread it into the patient's bone 5. This upper portion 9 also defines the threaded aperture 28 (shown in dashed lines in FIG. 2 and solid line in FIG. 5) that extends from the top surface 29, at the hexagonal projection 27, to the junction with the lower portion 10. Aperture 28 is used to connect the abutment 2 to the implant portion 9.

In a preferred embodiment, the implant's upper portion 9 may have a plurality of spherical projections 22 sintered to at least a portion of its exterior surface. The spaces between the spheres form micropores into which bone will grow. Preferably, the pores are between about 200 and 350 microns. The projections 22 are made of a material suitable for bone integration and should preferably be either a metal (e.g., titanium), a polymer, a composite, or a copolymer. Methods of sintering spherical projections, or beads, onto a metal's surface is generally known in the art. In particular, titanium bead sintering services have traditionally been provided by the FPD Company of McMurray, Pa. Sintering is also described in general in the *Encyclopedia of Chemical Technology*, Vol. 16, 4th ed., John Wiley & Sons (1995) at pp. 327–329, which is incorporated herein by reference.

Figure 6:
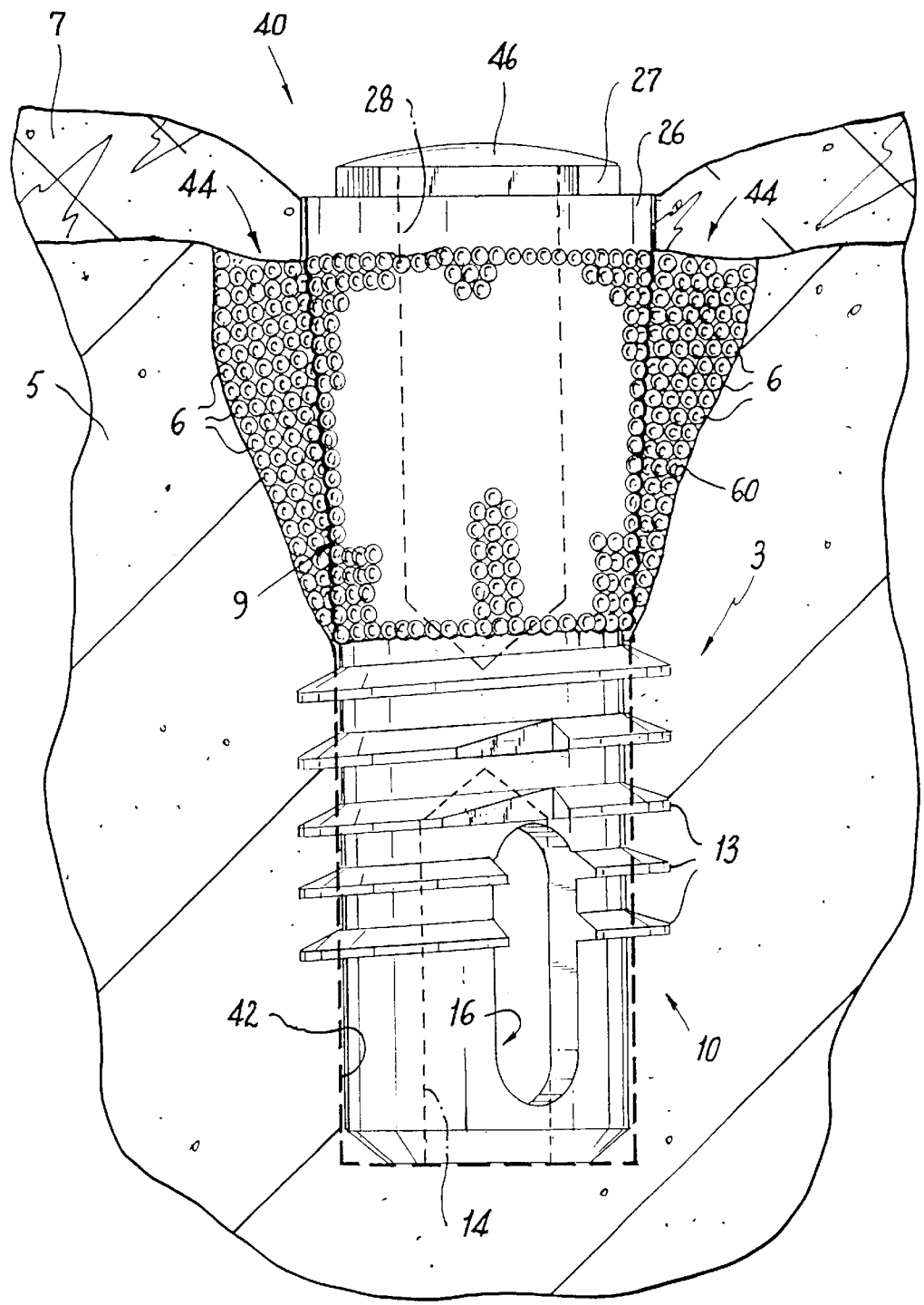
FIG. 6 illustrates the placement of the implant of the present invention in a tooth extraction site.

Just proximal to the vent 16, there is approximately 3 mm of thread that is designed so as to allow for immediate fixation within the bone to prevent movement of the implant. Thus, the implant 3 can be used for relatively immediate replacement of a tooth that has been removed. Shown in FIG. 6 is the general shape 60 of an extraction site 40. As this site is a cavity that is not cylindrical, it cannot be the site of a conventional cylindrical screw type implant unless bone is first regrown in the cavity and a new cylindrical bore is drilled in the new bone, a process that could take many weeks or months.

According to the installation process for use of the screw implant of the present invention, an incision is made in the gum tissue 7, if any, covering the extraction site to expose the underlying bone 5. Then, a small cylindrical bore 42 is drilled at the base of the conical extraction site 40. This bore 42, which is shown in dashed lines in FIG. 6, is made with about the diameter of the unthreaded part of the lower portion 10 of the implant 3. It is made deep enough so that the bottom two or three turns of the threads 13 can engage the bone surrounding the bore 42 at a level below the original bottom of the extraction site. The bone chips created during the formation of the bore 42 are preferably saved for later use.

According to the installation method of the present invention, the implant 3 is placed in the site 40 so the unthreaded portion rests in the bore 42. Then, using a wrench or similar tool engaged with the hexagonal projection 27, the implant is rotated. As a result, the cutting edge on lowest thread of the implant at the vent 16 engages the bone surrounding bore 42 and begins to self-tap into the bore. When the implant is rotated sufficiently, its base rests against the bottom of bore 42. Because the implant has been self-tapped into the bone, it is now firmly anchored at the implant site. Also, bone chips have fallen down or been pushed down the channel during this process. These chips have collected in the cavity 14 and will act to promote the growth on new bone in the cavity and through the vents to further anchor the implant in the future.

The space 44 between the rest of the extraction site 40 and the implant 3, especially about the upper portion 9, is now back filled with autogenous bone chips 6 saved from the creation of bore 42 or bone graft materials, such as bovine (xerographic) bone, synthetic bone (alloplastic, e.g., ceramic or plastic), allographic bone, or a combination thereof. This material may be resorbable or non-resorbable, solid or microporous. One synthetic bone material is disclosed in U.S. Pat. No. 4,728,570 of A. Ashman et al., and sold under the trade name Bioplant® HTR®. In addition, one or more bioactive substances that are medico-surgically useful may be incorporated into the synthetic bone. Various compositions of such are disclosed in U.S. Pat. No. 5,356,629 of Sander et al.

The bone graft material 6 is packed loosely so that it fills the voids along with the bleeding from the surgical site and makes intimate contact with the microbeads 22, which are preferably sintered titanium beads, on the surface of the upper portion 9. It may be advisable to use a surgical dressing to hold the bone chips in place. The dressing may be a surgical adhesive or glue, surgical foil, collagen, skin, or similar biocompatible material. In time, new bone will grow around and through the bone graft material 6, or replace it, thereby further anchoring the implant in place. This unique design of the implant 3 thus allows for immediate installation in a fresh tooth extraction site 40 and specifically addresses the requirements of extraction sites.

The implant design can permit either a single or two-stage installation. For a single-stage installation, the abutment 2 is installed during the initial installation of the implant. The abutment 2 extends through the sutured gum. The artificial tooth 4 may or may not be installed at the same time.

A two-stage or submergible implant is shown in FIG. 6. Once the bone graft material 6 is in place, a cap 46 is screwed into the threaded aperture 28 in the top of the implant to make sure the growth of new bone does not extend into the aperture. If bone does grow into this aperture, it can be very difficult to remove. Gingival tissue 7 is then sutured over the implant. Time is be allowed to pass so that new bone grows and firmly anchors the implant in place before the rest of the implant system is installed and the device is put into use.

At the second stage, the gingival tissue 7 is reopened. Often, bone has grown over the submerged implant and must be removed by a burr before the abutment 2 can be installed. However, if bone grows up over the edges of the collar 26, there is no need to remove it because it becomes part of the permanent abutment. The cap 46 is then removed from aperture 28 and replaced with the threaded shaft of an abutment 2. The threaded end of the abutment 2 is engaged with the threaded aperture 28 and is rotated so that it is firmly secured in the implant portion and is extending in the proper direction. With this firm attachment completed, the artificial tooth 4 can then be attached over the abutment cylinder 2.

Whether a single-stage or two-stage (submergible) procedure is used, the abutment 2, which may be straight or have an angled shaft, is selected so as to cause the artificial tooth 4 to be correctly aligned with the other teeth of the patient. Therefore, the dentist or oral surgeon must be provided with a variety of such abutments that are at standard angles.

Besides being used to mount a single tooth, the implants according to the present invention can be used as supports for a permanent bridge or a removable bridge.

While the invention has been particularly shown and described with reference to a preferred embodiment thereof, it will be understood by those skilled in the art that various changes in form and details may be made therein without departing from the spirit and scope of the invention.

We claim:

1. An implant for installation into a tooth extraction socket in the alveolar bone of a patient, comprising:
    an upper portion in the direction away from the bone when the implant is installed therein, said upper portion having an upper end tapered in said direction away from the bone, at least part of the upper end being adapted to promote bone integration and having a plurality of microbeads attached thereto;
    a lower portion in the direction toward the bone having a generally cylindrical shape, threads being located about at least a portion of said lower portion; and
    a channel extending through the threads, one side of the channel being at an angle up to a right angle with respect to the circumference of the periphery of the cylindrical portion and extending through the threads to create a cutting edge so that the threads are self-tapping.

2. The implant as in claim 1, further including a vent in said lower portion toward a bottom thread, the vent being aligned with said channel so that bone chips shaved off by the cutting edge can pass down said channel and enter the vent.

3. The implant as in claim 2, further comprising a plurality of said channels and said vents.

4. The implant as in claim 1, wherein the microbeads have been sintered to the upper end.

5. The implant as in claim 1, wherein the part of the upper end having microbeads attached thereto has a porosity of 200–350 microns.

6. The implant as in claim 1, wherein said channel widens from the top of said lower portion to the bottom of said lower portion.

7. The implant as in claim 1, wherein the microbeads are composed of a material selected from the group consisting of metals, polymers, copolymers and composites.

8. The implant as in claim 7, wherein the microbeads are titanium.

9. The implant as in claim 1, wherein the upper portion is generally convex in shape.

10. The implant as in claim 1, wherein the part of the upper end adapted to promote bone integration is positioned on the implant such that at least a substantial portion thereof is located in the extraction socket when the implant is installed.

11. The implant as in claim 10, wherein the upper portion is generally convex in shape.

12. The implant as in claim 11, wherein the microbeads have been sintered to the upper end.

13. An implant for installation into a tooth extraction socket in the alveolar bone of a patient, comprising:

a generally convex upper portion in the direction away from the bone when the implant is installed therein, at least part of the upper portion being adapted to promote bone integration and positioned on the implant such that at least a substantial portion thereof is located in the extraction socket when the implant is installed;

a lower portion in the direction toward the bone having a generally cylindrical shape, threads being located about at least a portion of said lower portion; and a channel extending through the threads, one side of the channel being at an angle up to a right angle with respect to the circumference of the periphery of the cylindrical portion and extending through the threads to create a cutting edge so that the threads are self-tapping.

14. The implant as in claim 13, wherein said channel widens from the top of said lower portion to the bottom of said lower portion.

15. The implant as in claim 13, wherein the part of the upper portion adapted to promote bone integration has a plurality of microbeads attached thereto.

16. The implant as in claim 15, wherein the microbeads have been sintered to the upper portion.

17. The implant as in claim 15, wherein the microbeads are composed of a material selected from the group consisting of metals, polymers, copolymers and composites.

18. The implant as in claim 17, wherein the microbeads are titanium.

19. The implant as in claim 15, wherein the part of the upper portion having microbeads attached thereto has a porosity of 200–350 microns.

20. The implant as in claim 13, further including a vent in said lower portion toward a bottom thread, the vent being aligned with said channel so that bone chips shaved off by the cutting edge can pass down said channel and enter the vent.

21. The implant as in claim 20, further comprising a plurality of said channels and said vents.

22. A method for installing a dental implant into a tooth extraction socket in the alveolar bone of a patient, the method comprising:

locating bone in an extraction socket;

creating a bore at a base of the extraction socket;

self-tapping an implant having self-tapping threads on a lower portion into the bone, said implant having an upper portion with an upper surface that is tapered in the direction away from the bone when the implant is installed therein, at least part of the upper surface being covered with an osteopromotive material;

back-filling, with a bone graft material, an area between the upper portion of the implant and the exposed extraction socket; and attaching an abutment with an artificial tooth to the upper portion of the implant.

23. The method for installing a dental implant as in claim 22, further including the steps of:

opening any tissue covering the extraction socket in order to locate bone in the socket;

positioning a healing cap on the upper portion of the implant after back-filling with bone graft material;

then covering the upper portion of the implant with tissue and allowing sufficient time to pass for bone to become integrated with the upper end of the implant;

then reopening the tissue after allowing time for new bone to grow before attaching the abutment.

24. The method for installing an implant as in claim 22, wherein the bone graft material is solid.

25. The method for installing an implant as in claim 22, wherein the bone graft material is microporous.

26. The method for installing an implant as in claim 22, wherein the bone graft material is resorbable.

27. The method for installing an implant as in claim 22, wherein the bone graft material is non-resorbable.

28. The method for installing an implant as in claim 22, wherein said step of back-filling the area created between the upper portion of the implant and the exposed extraction socket utilizes a bone graft material selected from the group consisting of autogenous, alloplastic, xerographic and allographic bone.

29. The method for installing an implant as in claim 22, wherein the osteopromotive material is a plurality of microbeads of a material selected from the group consisting of metals, polymers, copolymers, ceramics and composites.

30. The method for installing an implant as in claim 29, wherein the plurality of microbeads have been sintered to the outer surface of the upper portion of the implant.

31. The method for installing an implant as in claim 29, wherein the plurality of microbeads are composed of titanium.

32. The method for installing an implant as in claim 22, further including the step of using a surgical dressing to hold any bone chips in place after installation.

33. The method for installing an implant as in claim 32, wherein the surgical dressing is selected from the group consisting of biocompatible glue, surgical foil, collagen and skin.

34. The method for installing an implant as in claim 22, wherein the upper portion is generally convex in shape.

* * * * *